(12) United States Patent
Shadduck

(10) Patent No.: US 6,277,130 B1
(45) Date of Patent: Aug. 21, 2001

(54) ELECTRICAL DISCHARGE SURGICAL FASTENER FOR MENISCAL REPAIRS

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 0 days.

(21) Appl. No.: 09/461,501

(22) Filed: Dec. 14, 1999

(51) Int. Cl.$^7$ ................................................. A61B 17/04
(52) U.S. Cl. .................... 606/142; 606/143; 606/104; 606/219
(58) Field of Search .................... 606/104, 219, 606/139, 142, 143; 227/179.1, 19, 180.1

(56) References Cited

U.S. PATENT DOCUMENTS

| | | | |
|---|---|---|---|
| 4,488,523 | * 12/1984 | Shichman | 227/179.1 |
| 4,621,639 | * 11/1986 | Transue et al. | 606/215 |
| 4,724,840 | * 2/1988 | McVay et al. | 606/215 |
| 5,312,023 | * 5/1994 | Green et al. | 227/175.1 |
| 5,531,699 | * 7/1996 | Tomba et al. | 606/148 |
| 5,752,965 | * 5/1998 | Francis et al. | 606/151 |

* cited by examiner

Primary Examiner—Gary Jackson

(57) ABSTRACT

A surgical fastener system that utilizes a very intense electrical discharge in a captured fluid volume to cause fluid vaporization thereby to drive a fastener body distally from an open-ended channel in an introducer member. More in particular, the fastener system comprises proximal and distal fastener components that are carried in a channel in an introducer. The proximal fastener component is a fluid sealed in a volume proximal to the head of a fastener body. The distal component of the fastener system is the fastener body itself, which typically defines a head portion and extending leg portion. The system further provides a high voltage electrical source coupled to $1^{st}$ and $2^{nd}$ electrode terminations that are in substantial contact with the captured fluid volume. Upon actuation of a switch mechanism, an electrical discharge is induced between the $1^{st}$ and $2^{nd}$ electrodes which causes an intense thermal effect within the captured fluid which generates a vapor bubble therein. The explosive expansion pressures caused by such bubble formation thereby imparts driving forces against the fastener body to drive the fastener outwardly into or through the targeted structure. The driving force applied to the fastener head can be selected by controlling the power level of the electrical discharge.

21 Claims, 14 Drawing Sheets

ELECTRICAL DISCHARGE SURGICAL FASTENER FOR MENISCAL REPAIRS

FIELD OF THE INVENTION

This invention relates to a novel surgical fastener with an electrical discharge-based delivery system that allows for precise control of the momentum imparted to the fastener for penetration into or through tissue, for example into dense periosteal tissue or through captured tissue layers.

BACKGROUND OF THE INVENTION

In various orthopedic and general surgeries, it often is necessary to use penetrating-type implantable fasteners to secure tissue, cartilage, ligaments, sutures, mesh or other artifacts to perisoteum or other dense anatomic structures. A common procedure is the repair of a torn meniscus in which it is desirable to re-attach overlying portions of a torn meniscus to adjacent or underlying meniscus portions. One class of fastening device known in the art may be compared to a staple gun which uses a spring mechanism to drive a fastener distally from the device working end into the anatomic structure, or a reciprocating hammer to repeated drive the fastener. Also, various types deformable fasteners are used in surgeries to attach $1^{st}$ and $2^{nd}$ tissue layers, such as a biocompatible implantable staple. Such commercially available fastening instruments typically are designed to mechanically deform the malleable leg portions of a wire-form staple by holding a portion of the staple while bending leg portions as the staple is ejected from the distal working end of the instrument. A related type of fastener system captures tissue and drives a deformable fastener by means of a hammer mechanism into an anvil portion, as in an Endo-GIA or circular anastomosis stapler. The fastening instruments of all the types described above are mechanically complex and require many moving parts which results in relatively expensive instruments (e.g., from $100 to $300). Typically, such instruments must be disposable and thus add measurably to the costs of a surgery and cause financial burdens on the health care system.

Besides being expensive, the typical commercially available stapling systems suffer from several other disadvantages. First, a spring-driven mechanical fastener is propelled outwardly and into bone, periosteum, etc., with only a predetermined amount of force that in turn develops a particular rate of staple penetration. The rate may be too slow for the densest anatomic structure, often requiring repeated firings of staples until staple's depth of penetration is adequate. This may lead to time-consuming retrieval and removal of mis-fired staples. Also, the rate of staple penetration may be too fast for less dense anatomic structures leading to collateral tissue damage upon staple firing. When hammer-and-anvil type fastening mechanisms is employed, the thickness of captured tissue may vary widely. Such a system that develops a staple-driving force from a squeeze-type handgrip may not provide the operator adequate control over the power needed to propel the fastener through tissue layers. If the tissues are poorly fastened, for example in an intestinal anastomosis, the fastened site may leak and result in serious complications. Many tissue fastening procedures offer only a single opportunity to develop a secure or leak-proof seal. Another disadvantage of prior art fastener systems is that they cannot be scaled down in size to 2.0 to 5.0 mm. (or smaller) introducers for microsurgeries due to the mechanical complexity and moving parts of the device. Many of the above-described disadvantages relate to the unsophisticated means of delivering mechanical driving forces to the fastener—typically (i) a spring-load mechanism in the introducer or (ii) squeeze grips in a handle that mechanically translate driving forces to the fastener through a moving push-rod.

What is needed is: (1) a surgical fastener system that allows for precise control of the rate at which the fastener penetrates tissue; (2) a surgical fastener system that has very few moving thus making it inexpensive to manufacture; and (3) a surgical fastener that can be miniaturized and delivered from a substantially small introducer (e.g., 1.0 mm. to 3.0 mm. in diameter or cross-section). Besides, the above listed requirements, it would be desirable if the fastener system were suited for disposable introducers or non-disposable introducers.

SUMMARY OF THE INVENTION

The subjects and objects of this disclosure relate to novel surgical fastener systems that are adapted for developing penetrating forces based on the release of energy from an electrical discharge in a fluid captured in a chamber adjacent to a head portion of the fastener. The fastener typically is used for orthopedic procedures to attach tissue to periosteum etc., but may be also be used fasten tissue layers with a hammer-and-anvil type tissue-capturing and fastening system.

More in particular, the system comprises a first fastener component (or fastener body) that is configured with penetrating legs and a second fastener component (or driving component) that comprises a captured fluid volume just proximal to the head of the fastener body. In a typical embodiment, the fastener body and the captured fluid volume are sealably carried in an introducer working end having an elongate interior chamber with an open distal termination. The interior chamber portion containing the captured fluid volume carries $1^{st}$ and $2^{nd}$ electrode terminations that are connected to a remote high intensity electrical energy source. Upon actuation of a switch mechanism, an electrical discharge is induced between the $1^{st}$ and $2^{nd}$ electrodes to cause an intense thermal effect within the captured fluid volume to generate an explosive bubble (cf. such energy density also has been described as causing a cavitation bubble. The expansion pressures caused by the bubble formation thus will cause distal driving forces against the head of the fastener body to propel the fastener outwardly from the introducer and into or through the targeted structure. The driving force applied to the fastener head can be easily controlled by altering the power level of the electrical discharge. Moreover, the rate of fastener penetration can be further controlled by (i) adjusting the dimensions of the interior chamber and volume of captured fluid; and (ii) the dimensions between the $1^{st}$ and $2^{nd}$ electrodes. After firing a fastener with the electrical discharge, the only byproducts of the energy deposition in the fluid (e.g., sterile water) is water vapor which is compatible with the interior of the patient's body.

In general, the present invention is adapted to quickly and efficiently drive surgical fasteners in orthopedic procedures and other surgeries.

The present invention advantageously provides an introducer member that needs no moving mechanical parts for driving a fastener body.

The present invention advantageously provides a fastener system that utilizes electrical discharge (electrothermally generated) forces to drive a fastener body.

The present invention advantageously provides a fastener system that provides an electrical power controller for precisely varying the driving forces applied to a fastener body.

The present invention advantageously provides a fastener for micro-surgical procedures in which a fastener body can be scaled down to extremely small dimensions, e.g., 0.50 mm. to 1.0 mm. in diameter or cross-section.

The present invention advantageously provides an introducer portion that may be (i) highly elongate such as in a catheter, and/or (ii) deflectable or articulatable without detracting from the potential energy that may be applied to drive a fastener body from the distal working end of such an introducer.

The present invention advantageously provides a surgical fastener that may be constructed with relatively fragile bioabsorbable leg portions that may driven into dense structures by selectively high levels of momentum offered by the electrical discharge aspect of invention, wherein such relatively fragile bioabsorbable leg portions could not be driven by pounding with a prior art hammer-type delivery mechanism.

The present invention provides a fastener and delivery system that is both inexpensive and disposable.

Other objects and advantages of the invention will be apparent from the following description, the accompanying drawings and the appended claims. Additional advantages and features of the invention appear in the following description in which several embodiments are set forth.

DETAILED DESCRIPTION OF THE INVENTION

Figure 1:
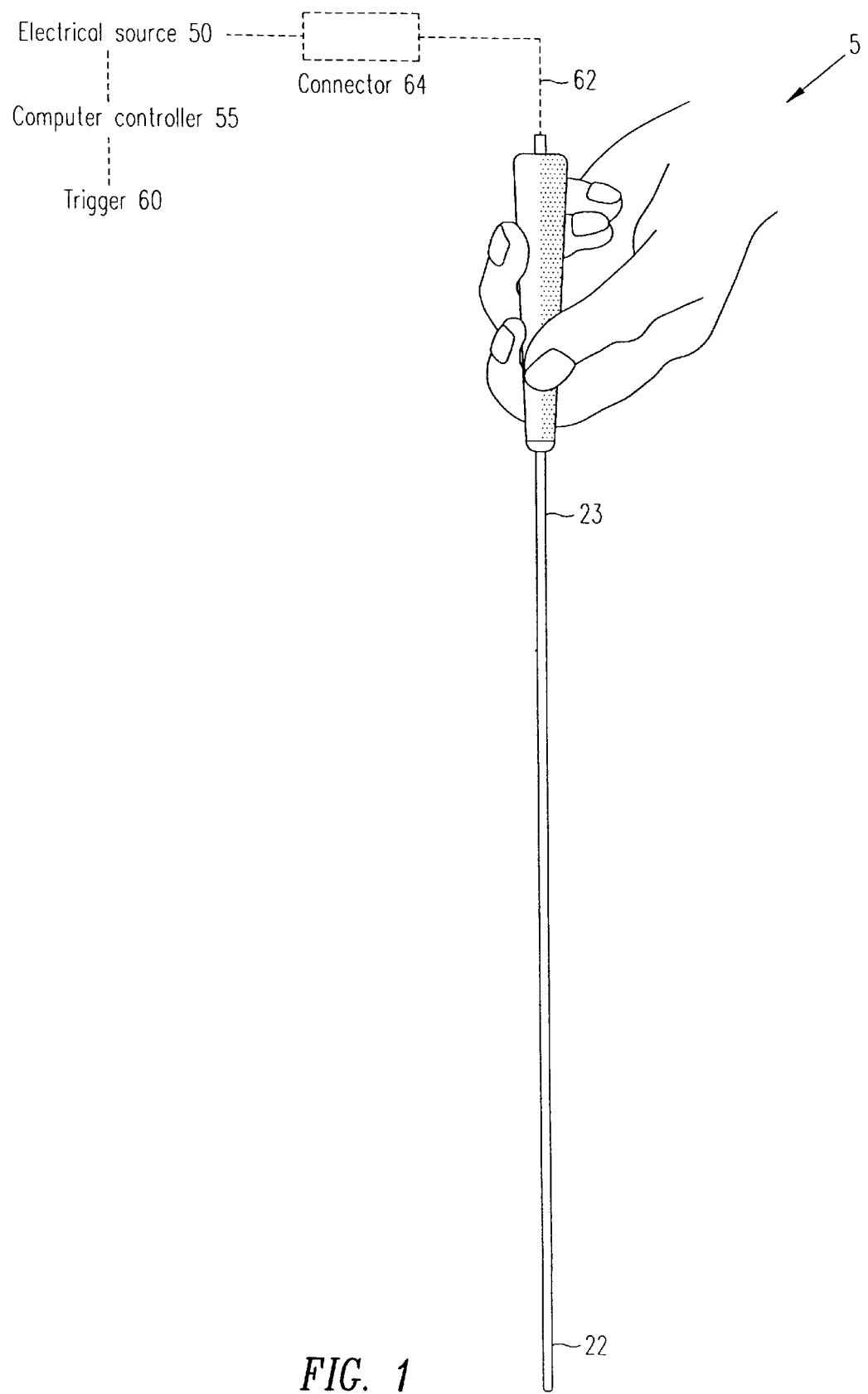
FIG. 1 is a plan view of a Type "A" single-fire fastener system in relation to a human hand.
Figure 2A:
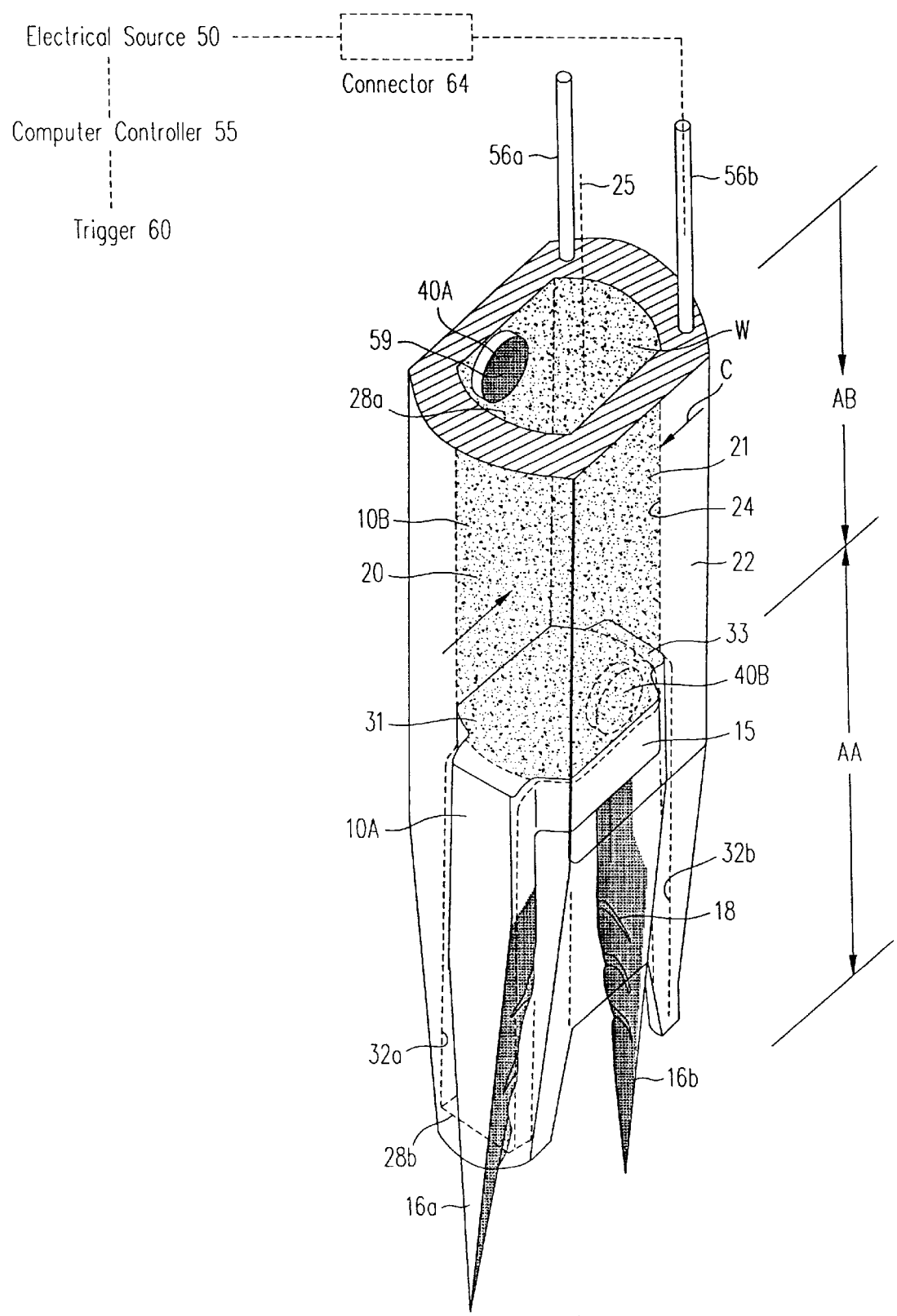
FIG. 2A is an axionometric view of a Type "A" fastener body component and a cooperating captured fluid component of the invention in a transparent introducer working end.
Figure 2B:
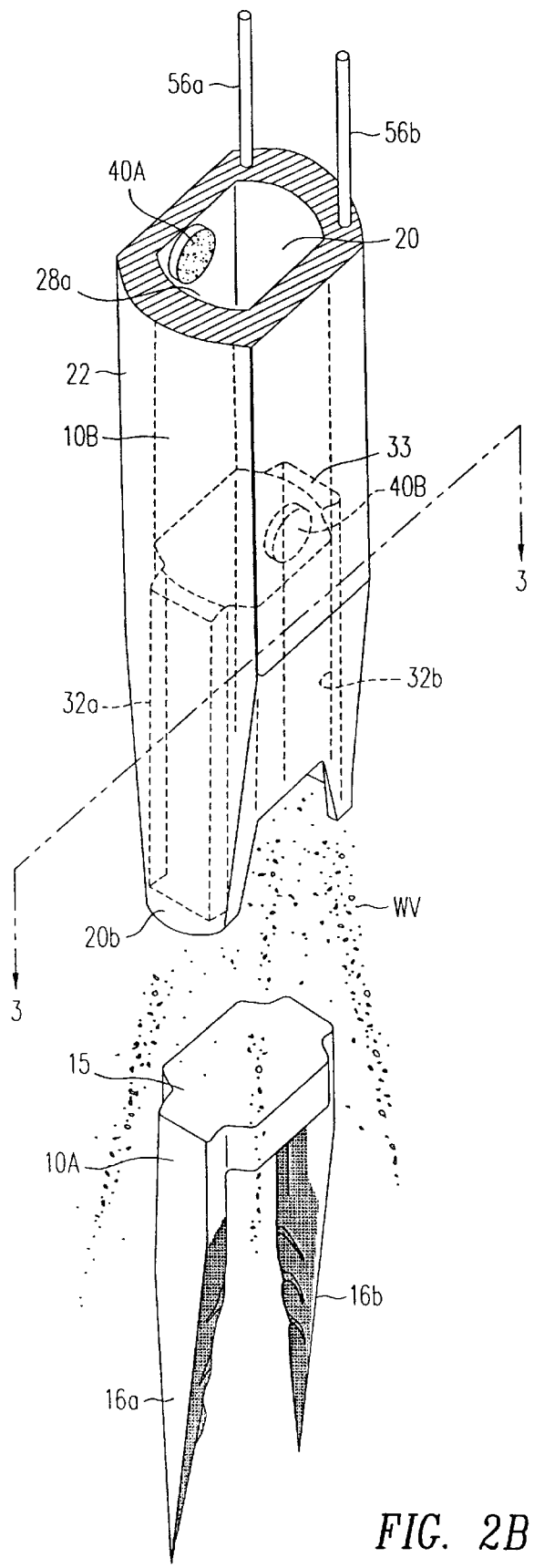
FIG. 2B is a view of the de-mated first and second components of the single-fire fastener system of FIG. 2A post-firing.

1. Type "A" Single-Fire Electrical Discharge Fastener System. FIG. 1 shows an exemplary Type "A" single-fire fastener system 5 that is adapted for fastening tissues, sutures or other similar anatomic structures, and is particularly suited for mensical repairs. The exemplary system of FIG. 1 may be small in diameter, e.g., about 1.0 to 5.0 mm. in diameter and used for re-attaching torn meniscus portions in a common form of meniscal tear. Referring to FIGS. 2A–2B, the Type "A" embodiment of the invention provides first and second fastener system components (i.e., fastener body portions 10A and cooperating fluid chamber portion 10B). Best seen in FIG. 2B, the fastener body portion indicated at 10A has a proximal head section 15 and extending therefrom an extending section (or penetrating section) indicated at 16 that comprises at least one extending element (or penetrating leg), in this case two leg elements 16a and 16a. It should be appreciated that the number of penetrating elements may vary from one to several and a preferred fastener has two legs for mensical repairs. The at least one leg may be smooth and preferably has gripping barbs of any sort as indicated at 18 in FIGS. 2A–2B.

The penetrating leg elements 16a and 16a are of any suitable biocompatible implantable metal (e.g., titanium, stainless steel) or any suitable biocompatible polymer (or composite metal and polymer) which can be engineered to have a sufficient strength to accomplish the objective of penetrating tissue without unwanted deformation while being driven in the manner described below (e.g., a polymer such as Delrin® polyacetal available from DuPont). The legs may also be a composite of metal and polymer. The force required to penetrate tissue may be small and partly dependent on the cross-section of the penetrating legs, and the configuration or sharpness of the tip of each leg 16a and 16a. The head portion of the fastener may be flat or crowned and the head and leg elements may optionally be of any suitable bioasorbable material known in the art, such as polylactic acid (lactide), polygloycolic acid (glycolide) as disclosed in U.S. Pat. No. 3,739,773 (Schmitt, et al.), or co-polymers disclosed in U.S. Pat. No. 4,340,565 (Rosensaft, et al.) and U.S. Pat. No. 4,429,080 (Casey, et al.), all of which are incorporated herein by reference. Other bioabsorbable materials are known, such as dioxanone, caprolactone, trimethylene carbonate, and mixtures thereof which also may be suitable.

FIGS. 2A–2B further show that the first system component or fastener body 10A is sealably coupled to the second system component 10B which carries the captured fluid volume 21 prior to firing. More particularly, in this Type "A" embodiment, the second system component comprises a fluid-containing structure 10B that defines a proximal fluid-tight chamber 20 (and captured fluid volume 21 therein) that is carried at the working end 22 of an elongate introducer 23. The proximal fluid-tight chamber 20 is aligned and communicates with an elongate distal chamber portion 24 that extends along axis 25 from its proximal end 28a to distal open termination 28b. As can be seen in FIGS. 2A–2B, fastener body 10A has a selected overall axial dimension AA. When the fastener 10 is slidably positioned within chamber portion 24 as shown in FIG. 2A, the fluid-tight chamber indicated at 20 having axial dimension AB is defined between the proximal end 28a of fluid-tight chamber 20 and the surface 31 of head section 15 of the fastener. This fluid-tight chamber 20 is filled with a water W or any other suitable biocompatible fluid, wherein fluid is defined as any flowable material (liquid, gel, gas) and preferably is sterile water or hydrogel. (A hydrogel may be preferred to reduce evaporation during storage of the system; a gas is less preferred due to its compressibility).

Figure 3:
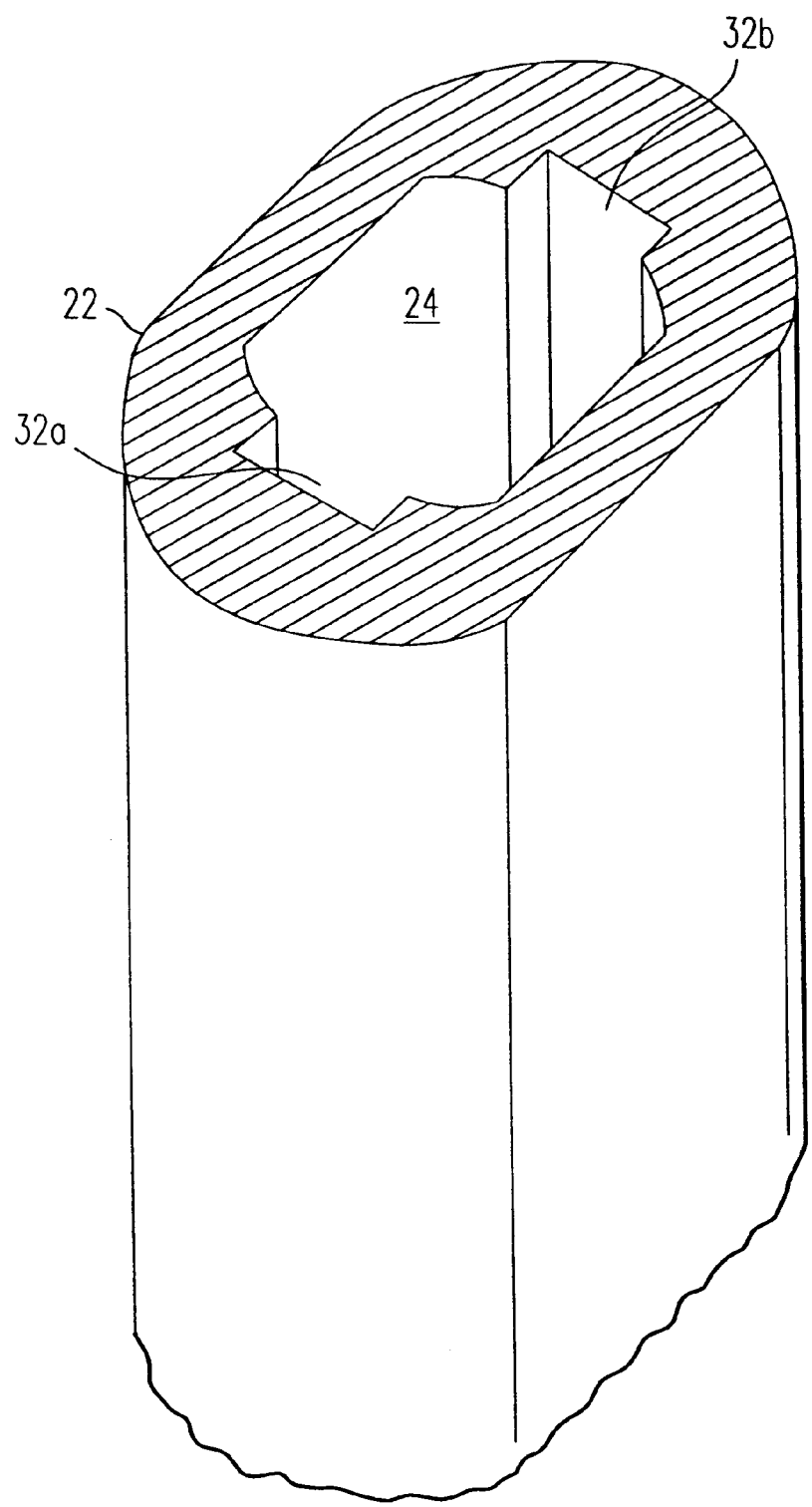
FIG. 3 is a sectional view of a component of the fastener system of FIGS. 2A–2B taken along line 3—3 of FIG. 2B.

In the exemplary embodiment of FIGS. 2A–2B and 3, it can be seen that leg elements 16a and 16a of body 10A are adapted to slide within channel portions 32a and 32b of the interior chamber 24 and head portion 15 of the fastener is adapted to slide within central portion 34 of chamber 24. The interface between the fluid-tight chamber 20 and distal chamber portion 24 is shown with an optional abutment face 33 that is adapted to contact the head portion 15 of body 10A to prevent the fastener body from being slid proximally into fluid-tight chamber 20 thereby fixing the volume of the fluid-tight chamber (see FIG. 2A). It should be appreciated that the cross-section of fastener body 10A and interior chamber 24 in which the fastener slides may be of an suitable configuration for cooperative and slidable mating and fall within the scope of the invention (see FIG. 3). As can be seen in FIG. 2A, a preferable mating of fastener body 10A to working end 22 is to have the sharp tips of the fastener legs slightly protrude from the introducer 23 for engaging a targeted structure before firing the fastener. The fastener body 10A is dimensioned to slide axially within interior chamber 24 easily yet create an effective seal to maintain the captured fluid volume 21 in fluid-tight chamber 20. Any suitable form of sealant may also be used to maintain water W sealed in chamber portion 20, in which case the strength of any such sealant will be overcome by rapid distal movement of the fastener from distal chamber portion 24 as described below.

Turning again to FIGS. 2A–2B, paired $1^{st}$ and $2^{nd}$ electrodes 40A and 40B are shown having exposed terminations in proximal chamber 20. FIG. 1 shows high-voltage electrical energy source 50 and power level controller indicated at 55 which are coupled to $1^{st}$ and $2^{nd}$ electrodes 40A and 40B by conductive wire leads 56a and 56b. The introducer portion 20 may be of any suitable insulated material such as a plastic, ceramic, glass or a combination of separate elements as are known in the art. The diameter or cross-section C of proximal fluid-tight chamber 20 may be from about 0.50 mm. to about 10.0 mm. or more and preferably is from about 1.0 mm. to 5.0 mm. The length AB of chamber 20 along axis 25 is from about 1.0 mm. to about 20.0 mm., and preferably is from about 2.0 mm. to 5.0 mm. The proximal end 28a of chamber 24 may be any shape and may preferably be hemispherical (not shown). The introducer 23 preferably is of a transparent material (e.g., polycarbonate) to view system, for example to see if the system is loaded (which will be more important in the multi-fire systems described below).

Referring to FIGS. 2A–2B, the electrical source 50 is adapted to deliver an intense electrical discharge within fluid-tight chamber 20 between the paired electrode arrangement, with such electrodes typically positioned proximally and distally on opposing sides of chamber 20. The exemplary $1^{st}$ and $2^{nd}$ conductive electrodes 40A and 40B are of any suitable conductive material. In accordance with the practice of the invention, the $1^{st}$ and $2^{nd}$ electrodes 40A and 40B may have active surface portions with a particular surface geometry or shape that is adapted to enhance the intensity of the electric discharge and the energy density within the fluid at the time of energy delivery. For this reason, such surface geometry preferably may include at least one projecting edge or varied sharp edge portions on the active electrode surfaces (not shown). It should be appreciated such preferred surface geometry may include a ridged electrode surface, or a plurality of micro-scale sharp edges that may be characterized simply as surface roughness on the active surface of the electrode, and as such may be provided by any suitable chemical, electrochemical or abrasive method to create the micro-edges or asperities indicated at 59.

The controller 55 is operatively connected to electrical source 50 to control the power level setting as well as to receive signals from a trigger mechanism 60 for activation of the electrical discharge, in response to a signal from the system operator. Any sort of on-off trigger switch 60 (preferably a foot-switch or finger switch in introducer 23 (not shown)) is connected to controller 55 and provides an activation signal in response to the actuation of the switch. The power level setting may be set by the operator by a form of rheostat-type control within controller 55. By adjusting the power level, the operator vary the driving forces applied to the fastener body. The electrical source 50 is of a type known in the art that is capable of delivering high intensity electrical current, for example in the range of 50 to 10,000 volts. It is estimated that the preferred voltage applied between the $1^{st}$ and $2^{nd}$ electrodes 40A and 40B will be in the range from about 50 to 2,000 volts, which is dependent on the volume of water W in fluid-tight chamber 20 that must be heated to form a vapor bubble therein. A power cable 62 is detachably coupled to the fastener system at connector 64 which carries electrical current to the two wire leads 56a and 56b. Thus, the introducer portion 23 of this Type "A" embodiment (optionally along with wire leads 56a and 56b) can be disposable after a single use since it is very inexpensive.

Figure 4A:
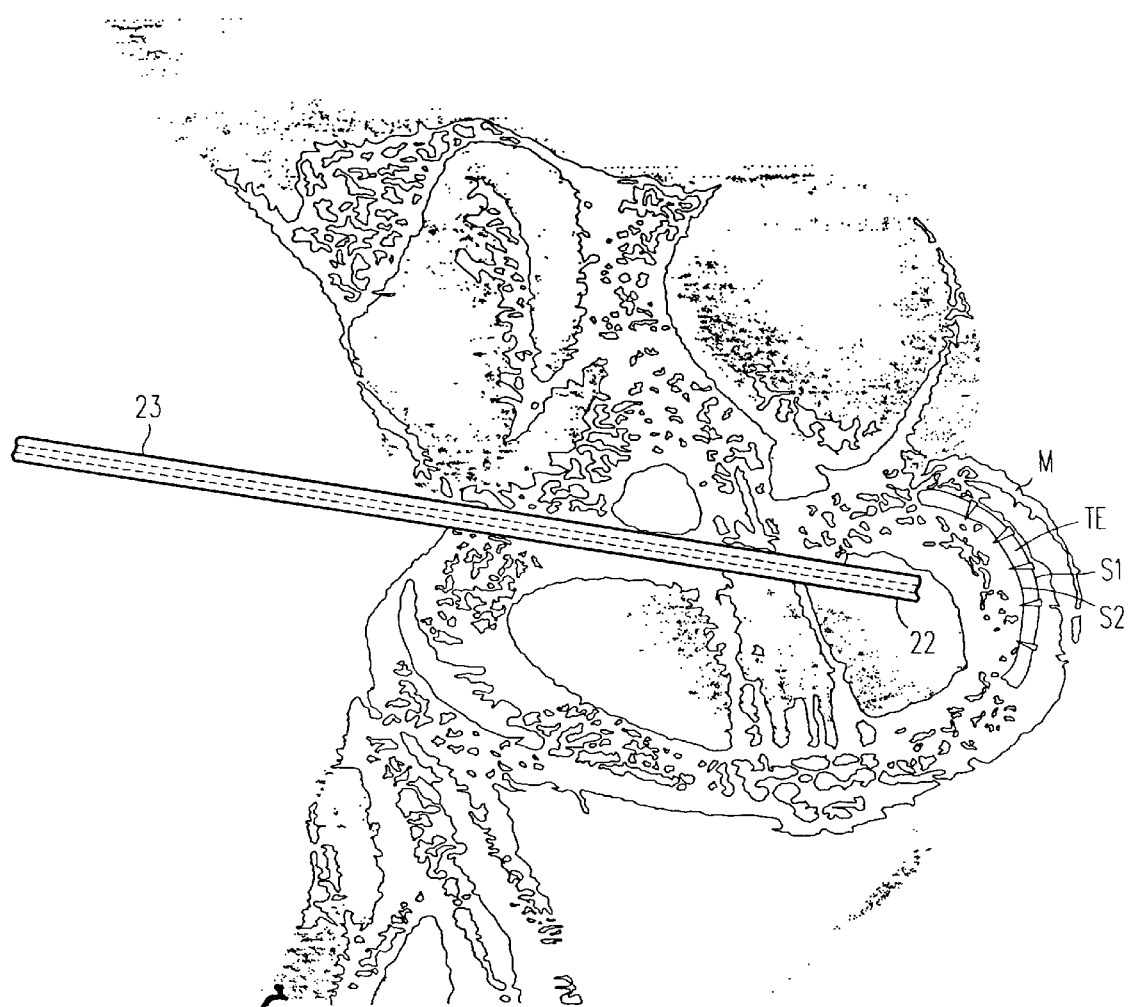
FIG. 4A is a view of a method of using the fastener system of FIGS. 1–3 to perform a method of the invention in repairing meniscal tear.
Figure 4B:
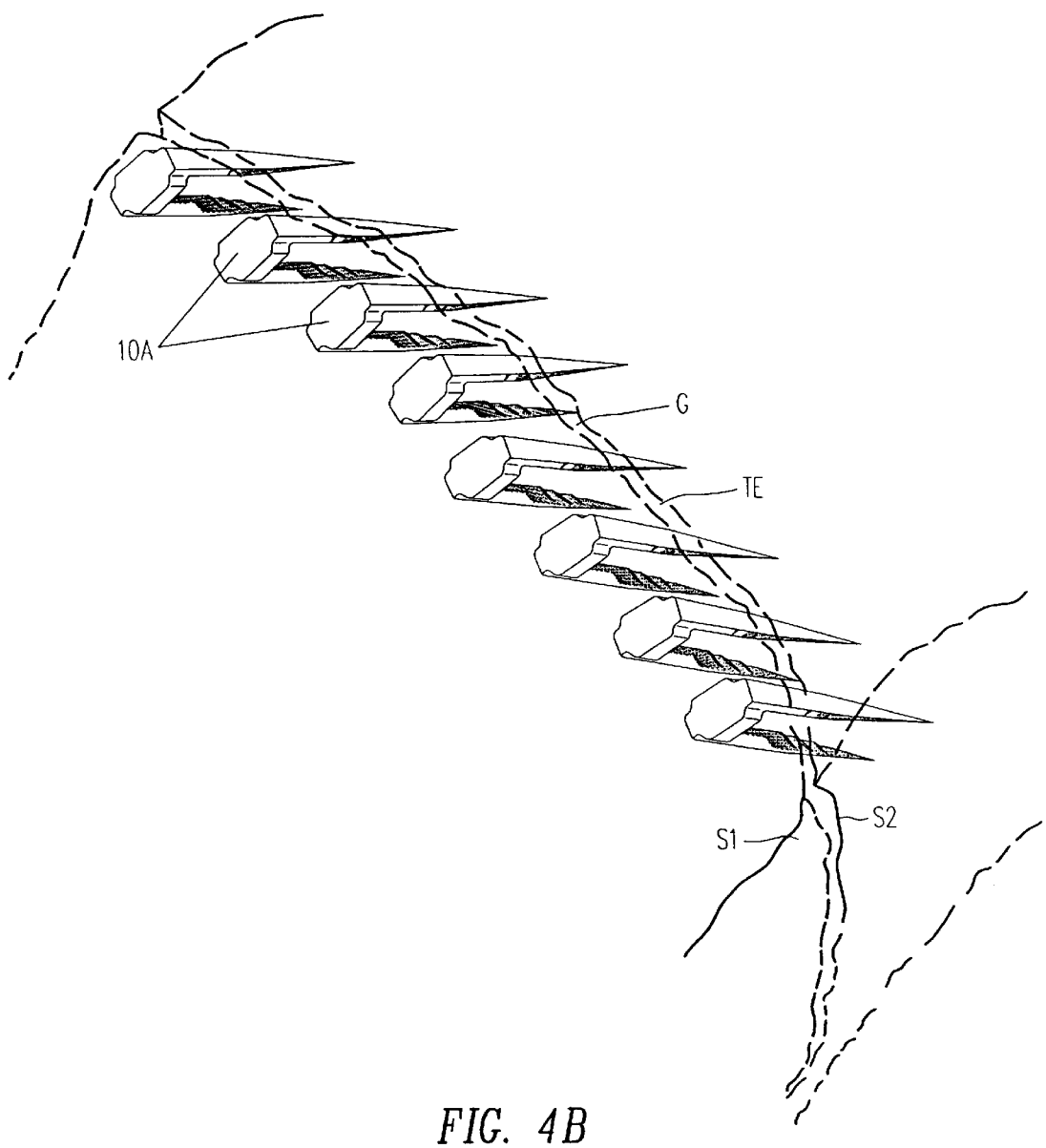
FIG. 4B is an enlarged view of the method of using the fastener system of FIG. 6A to provide multiple microfasteners to closely approximate the sides of a meniscal tear or other type of tissue attachment.

In a method of operation of the invention, referring again to FIG. 2B, an electrical discharge in proximal fluid-tight chamber 20 with the fastener body 10A carried within distal chamber 24 will instantly develop a vapor bubble within the captured fluid volume 21 and the very high pressure caused by the bubble formation and expansion will eject fastener 10A from the distal end 28b of distal chamber 24 (along with harmless water vapor WV) and into the targeted anatomic structure. FIG. 4A shows a method of utilizing the fastener system 5 to fasten a common form ("bucket handle" type) of tear TE in a patient's meniscus M. A particular advantage of the system for mensical repairs is that a large number (e.g., from 5 to 20) of bioabsorbable micro-fasteners of the type shown in FIGS. 2A–2B may be used to re-attach torn portions of the meniscus so that any gap G in the tear TE is minimized (see FIG. 4B). It has been found that mensical tears are very difficult to heal due to the lack of blood supply to large portions of the meniscus. It should be appreciated that the length of the legs in the fastener body 10A in FIG. 4B are not to scale, and preferred legs may be up to 15 mm. to 20 mm. in length. It is believed that a tight closure of sides S1 and S2 of the tear TE with multiple bioabsorbable micro-fasteners will optimize the opportunity for complete healing of the tear (see FIG. 4B). In contrast, the prior art mechanically-driven fasteners used for mensical repairs are quite large and only one or two are used per repair which may not closely approximate the edges of the tear to allow healing. It is believed that an electrical discharge in the range of 50 to 2,000 volts, depending on the cross-section, length and mass of the fastener, will cause an instantaneous velocity in the range of from about 5 to 250 m/s, and the substantial momentum imparted to the fastener by such a system will allow for optimal penetration characteristics. It should be appreciated the use of a plurality of micro-fasteners at multiple sites also will be useful for attaching meniscal implants (or other grafts) which are in development by several companies and are known in the art.

Figure 5A:
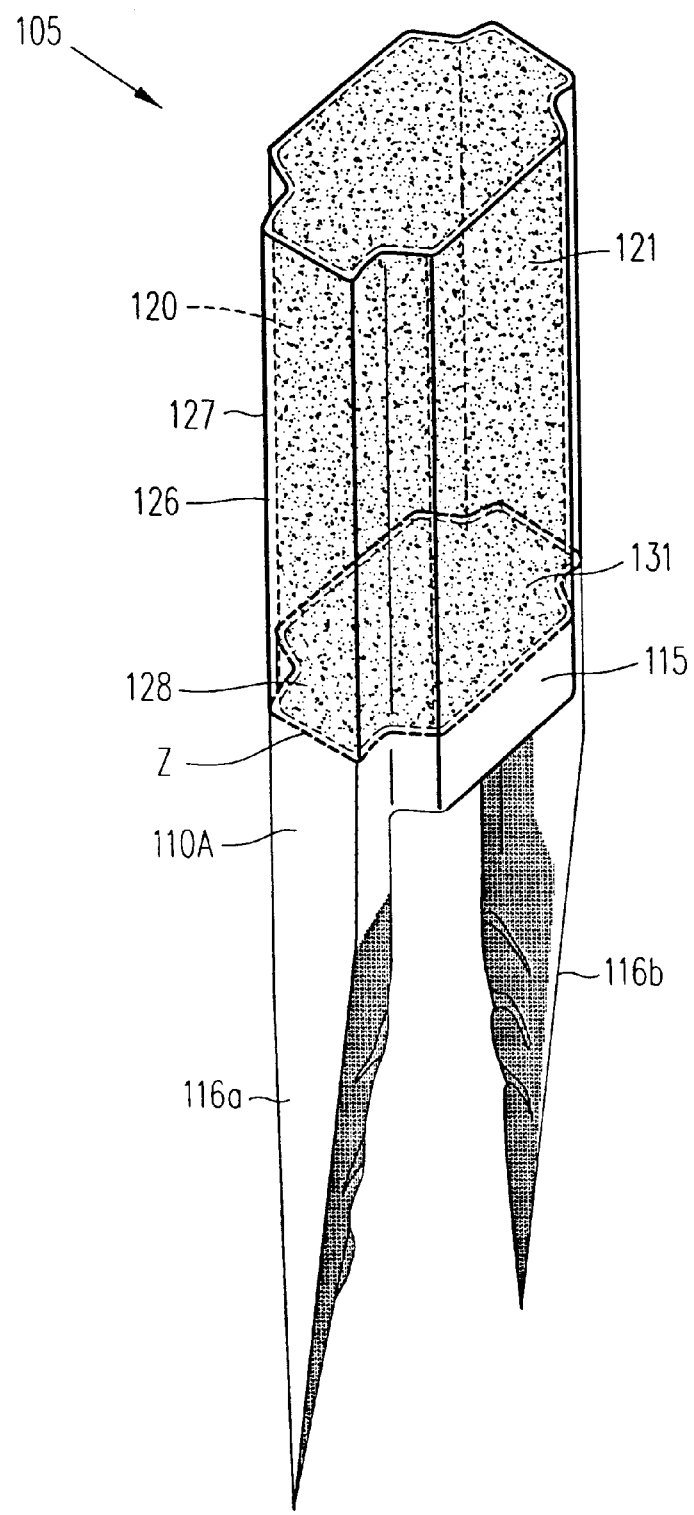
FIG. 5A is an axionometric view of a Type "B" fastener body and a cooperating captured fluid component.
Figure 5B:
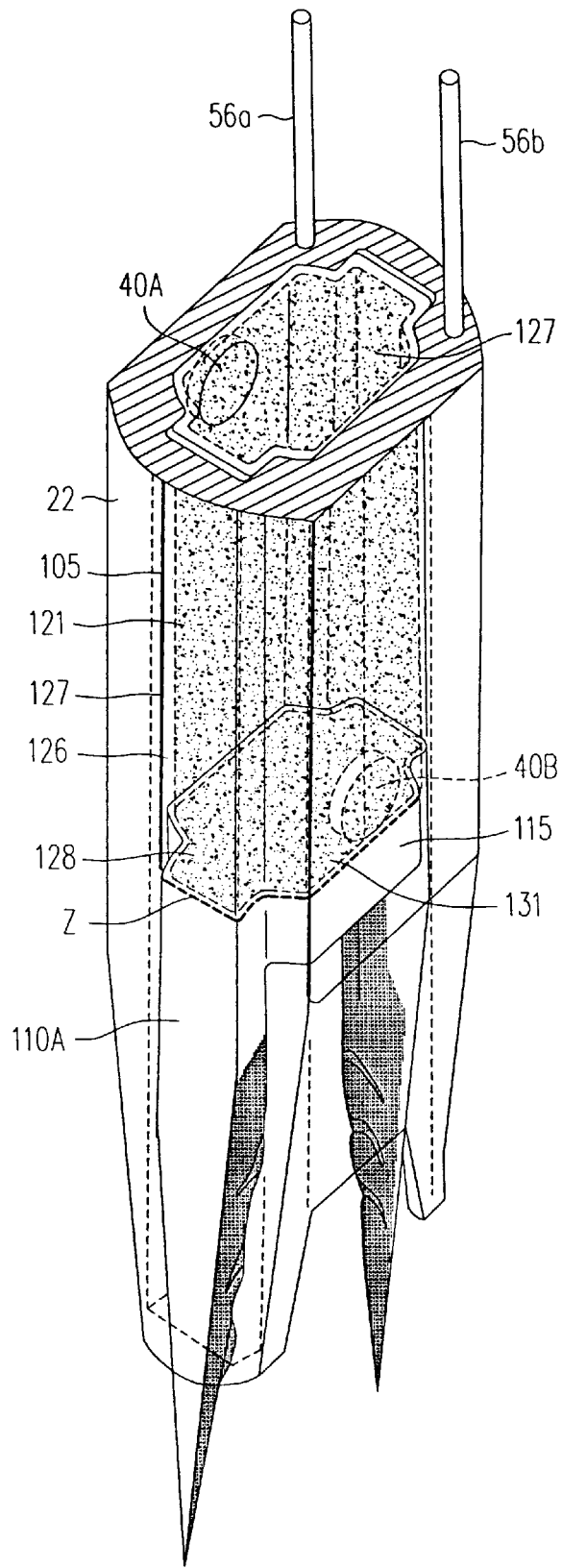
FIG. 5B is a view of the Type "B" fastener body of FIG. 5A in a pre-fire position in an introducer member.

2. Type "B" Electrical Discharge Fastener. FIGS. 5A–5B show an exemplary Type "B" self-contained fastener body 105 that operates in accordance with the above-described electrical discharge principles. The elements of this Type "B" fastener that correspond to similar elements of the Type "A" embodiment have the same reference numeral with the addition of 100. Elements that are identical may have the same reference numeral. This Type "B" fastener generally is adapted for use in an introducer member 23 that is reusable.

As can be seen in FIG. 5A, this embodiment has a fastener body 110A with head portion 115 and legs 116a and 116b. The captured fluid volume 121 in this embodiment is carried in an interior chamber 120 that is coupled to a fastener body 110A. The interior chamber 120 is defined within the walls 126 of a proximal fastener section 127 that is sealably and detachably mated to head portion 115 of the fastener body along interface 128 at the proximal surface 131 of the fastener head 115. While there are many manners of detachably mating the walls 126 of the proximal fastener section 127 to the fastener body 110A that fall within the scope of the invention, a preferred manner is to unitarily mold the wall to 127 to head 115 or to cement the walls 127 to head 115 when both portions are of a plastic-like bioabsorbable composition as described previously or any other biocompatible dissolvable material that will dissolve in the patient's body. Then, a break-away weakened-plane zone indicated at Z may be provided generally about the interface 128 to allow that portion to fracture or pulverize upon on explosive electrical discharge across chamber 120 and within the captured fluid volume 121.

Figure 6:
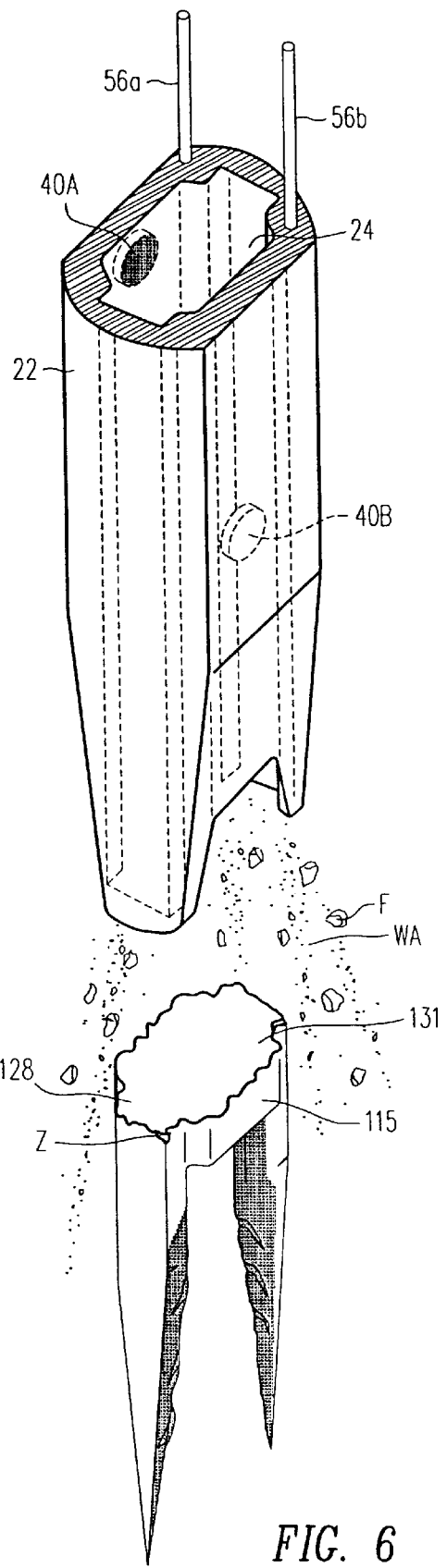
FIG. 6 is a view of the Type "B" fastener body of FIG. 5B post-firing.

In a method of operation, this Type "B" embodiment is inserted into an introducer member 23 having a working end 22 and channel 24 that is substantially identical to the previously Type "A" introducer (see FIGS. 2A–2B) except that the that working end is dimensioned to receive the Type "B" proximal fastener section 127 mated to fastener body 110A. As can be understood from FIG. 5B, however, in this case the electrodes 40A and 40B are not directly exposed to the captured fluid volume 121. Instead, the electrodes are in direct contact with the thin wall 126 the proximal fastener section 127. In this embodiment, the electrical source 50 is capable of generating sufficiently high energy densities between the electrodes 40A and 40B to vaporize the captured fluid volume as well as de-mate fastener body 110A from the proximal fastener section 127 generally along interface Z. As can be seen in FIG. 6, the explosive power of the vapor bubble formation preferably fracture and pulverize the entire thin wall 126 of the proximal fastener section 127 and expel the fragments F along with water vapor WV. It is for this reason that the proximal fastener section 127 is preferably made of bioabsorbable material as the fragments F can be left in the interior of the patient's body to dissolve. (Whereas many surgical fastening procedures may allow dissolvable fragments F in the body for a short period of time, some procedures such as in a joint capsule may not tolerate such fragments F.) An advantage of this type of self-containing fastener body 105 is that a wide variety of fasteners with (i) different fastener head shapes, (ii) different fastener leg types as well numbers of legs, (iii) different options of biocompatible or bioabsorbable fastener portions, and/or (iv) differing volumes of captured fluid may be provided for use with a single type of introducer 23.

Figure 7:
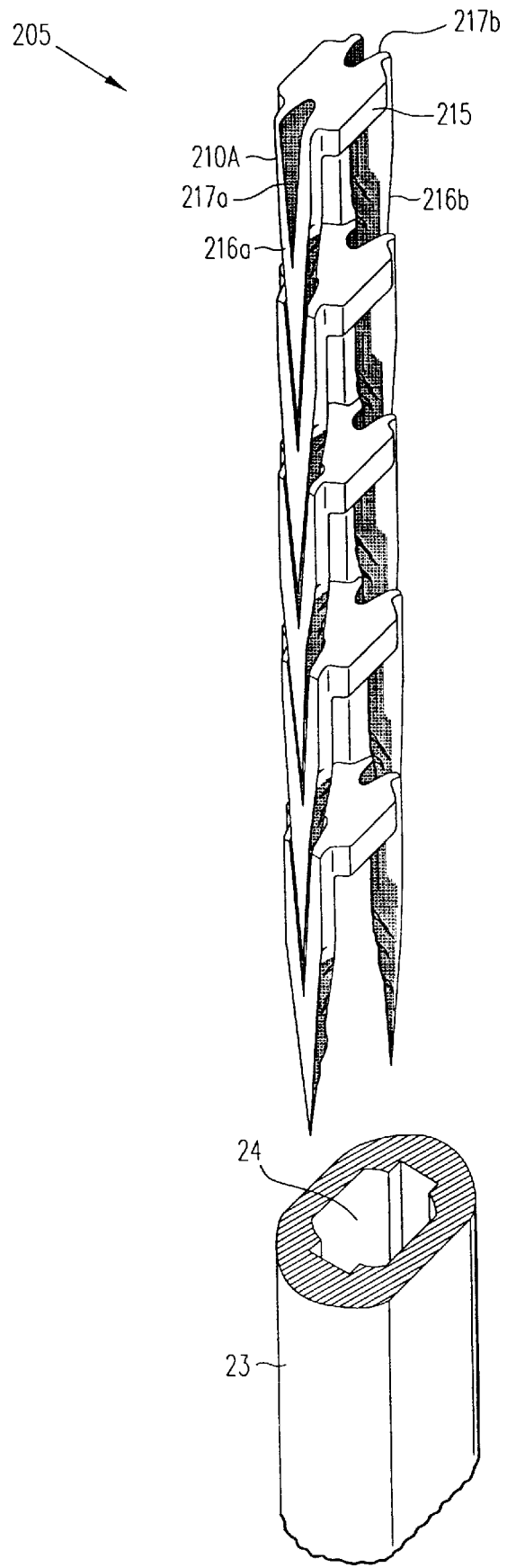
FIG. 7 is an axionometric view of a series of Type "C" fastener bodies in a stacked arrangement.
Figure 8:
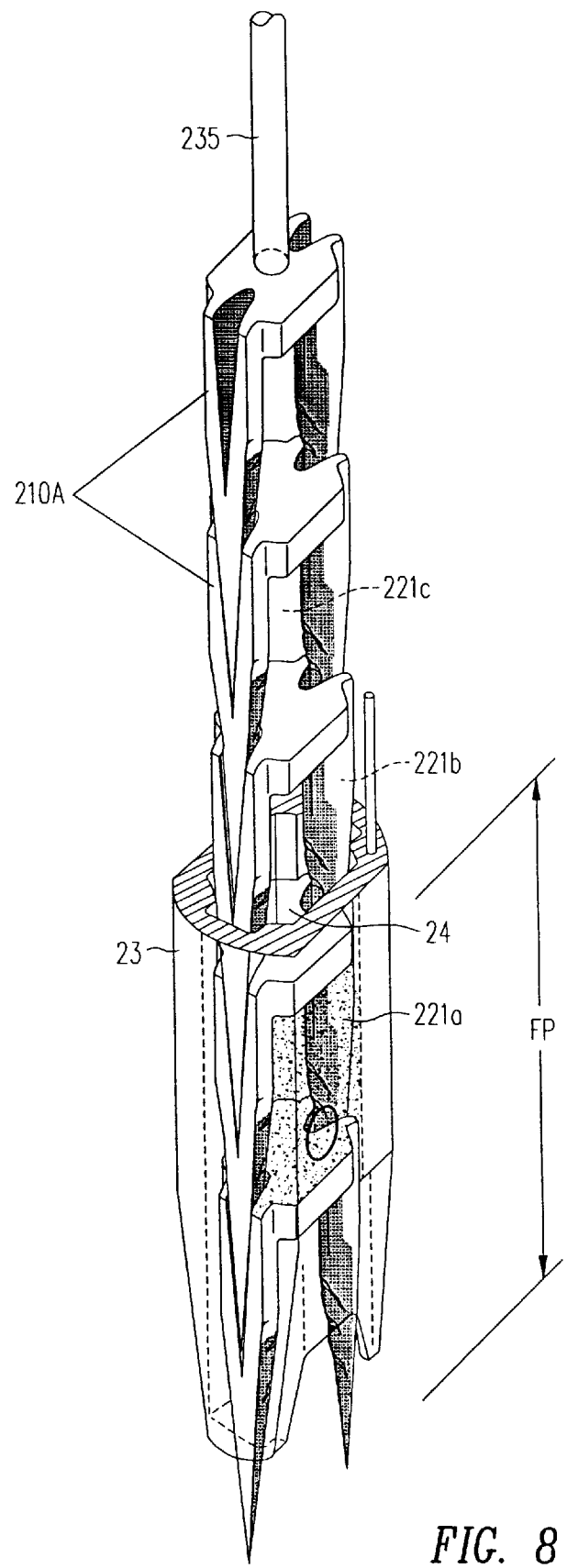
FIG. 8 is a view of the Type "C" fastener body of FIG. 6 in a pre-fire position in an introducer member.
Figure 9:
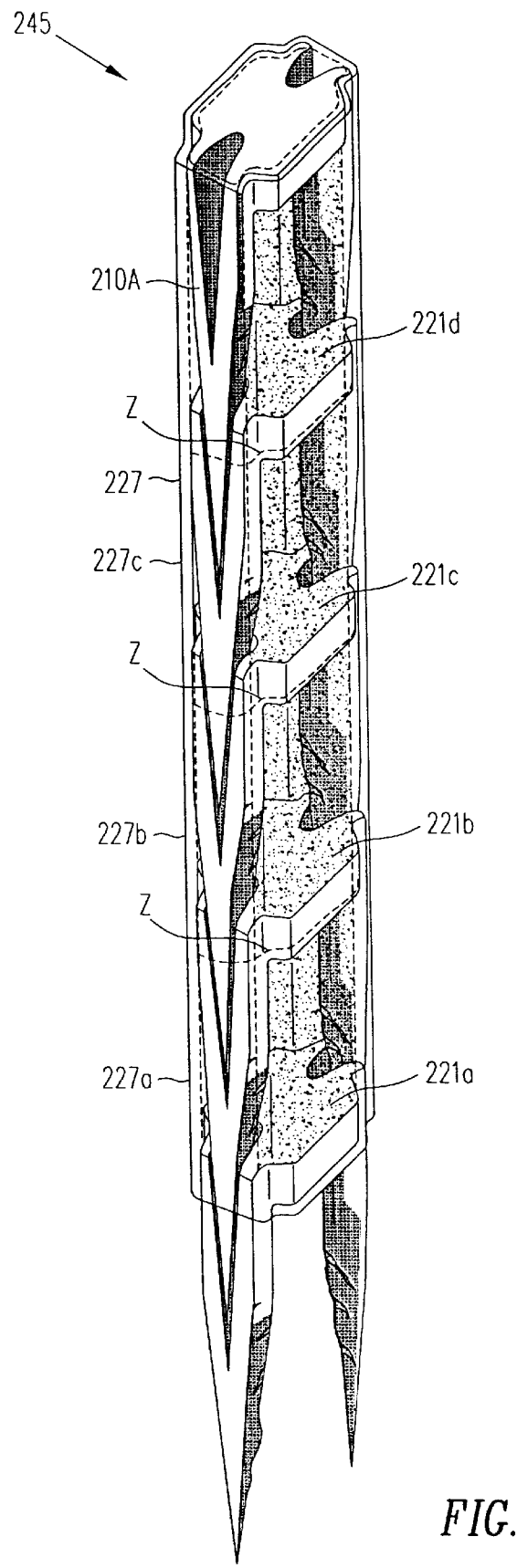
FIG. 9 is an axionometric view of a cartridge containing a plurality of Type "C" fastener bodies.

3. Type "C" Multi-Fire Electrical Discharge Fastener. FIGS. 7–9 show exemplary Type "C" embodiments of fastener systems 205 that are similar to the Types "A" and "B" embodiments except that they are adapted for multiple fastener loading of an introducing member. The elements of these Type "C" fastener systems that correspond to similar elements of the Types "A" and "B" embodiments have the same reference numerals with the addition of 200. Elements that are identical to previous embodiment have the same reference numeral. In this embodiment, the Type "C" fastener cartridges may be adapted for use in a disposable or reusable introducer member 23.

In general, the surgical fastener in FIG. 7 is similar to previously described embodiments with the fastener body indicated at 210A with head portion 215 and legs 216a and 216b. In this embodiment, a plurality of fastener bodies 210A may be assembled into a stack by at least partially sealably nesting with one another in a longitudinal manner in channel 24 in the introducer member (see FIG. 8). In the exemplary embodiment shown in FIG. 7, each leg 216a and 216b fits into to a cooperatively dimensioned recessed groove 217a and 217b in the head and leg of each fastener. It can be easily understood how each fastener can have from one to three or more legs and sealably nest with another in a cooperating channel 24 of an introducer. Now turning to FIG. 8, it can be seen how a series of fasteners 210A are loaded in an introducer with a plurality of captured fluid volumes 221a . . . 221n just proximate to the head 215 of each fastener. This multiple-fire version of the invention provides an actuatable push-rod 235 that is adapted to move axially to move each fastener body 210A to the firing position indicated at FP in FIG. 8. In this exemplary embodiment, each captured fluid volume 221a . . . 221n is adapted to advance axially along with the fastener bodies, and for this reason a viscous fluid may be desirable to prevent its escape into channel 24. The system may alternatively provide fluid inflow channel (not shown) in the introducer 23 to replenish or provide a captured fluid volume and fall within the scope of the invention. The push-rod 235 is actuatable from a proximal handle end (not shown) of the introducer 23 by an mechanism known in the art, of which many are known and therefore not necessary to detail herein. Thus, when each fastener body 210A is advanced axially to the firing position FP (see FIG. 8), the electrodes will be adjacent to and in contact with the captured fluid volume 221n just proximal to the head 215 of the distalmost fastener body within channel 24. The manner and effect of firing the fastener is the same as illustrated in FIG. 2B.

FIG. 9 illustrates a slight variation on the Type "B" single-fire fastener embodiment—this time adapting it for a multiple-fire cartridge indicated at 245. In this case, a plurality of fastener bodies indicated at 210A with head portions 215 and legs 216a and 216b are stacked as described previously. However, the fastener bodies each are captured by a fastener sleeve 227 (collectively) that sealably maintains the captured fluid volumes 221a . . . 221n along with the fastener bodies in the cartridge 245. The fastener sleeve portion 227 is made up of a plurality of sleeve sections 227a . . . 227n that contain each captured fluid volume 221a . . . 221n and are adapted to separate from an adjacent section along a de-mating zone Z that is similar to that described in the Type "B" embodiment above. In operation, it can be easily understood how fastener cartridge 245 can be operated similar to that shown in FIG. 8, and the firing of each fastener would be indicated to that depicted in FIG. 6.

Figure 10A:
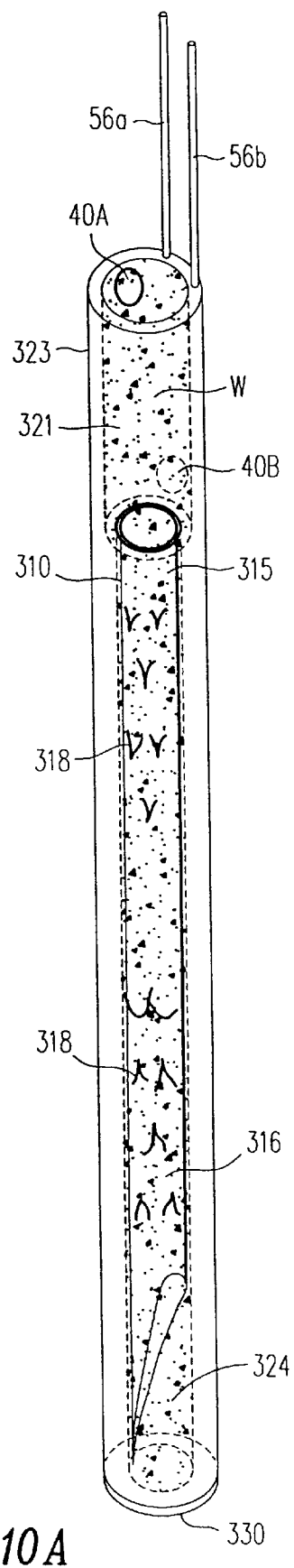
FIG. 10A is a view of the Type "D" arrow-type fastener body in a pre-fire position in an introducer.
Figure 10B:
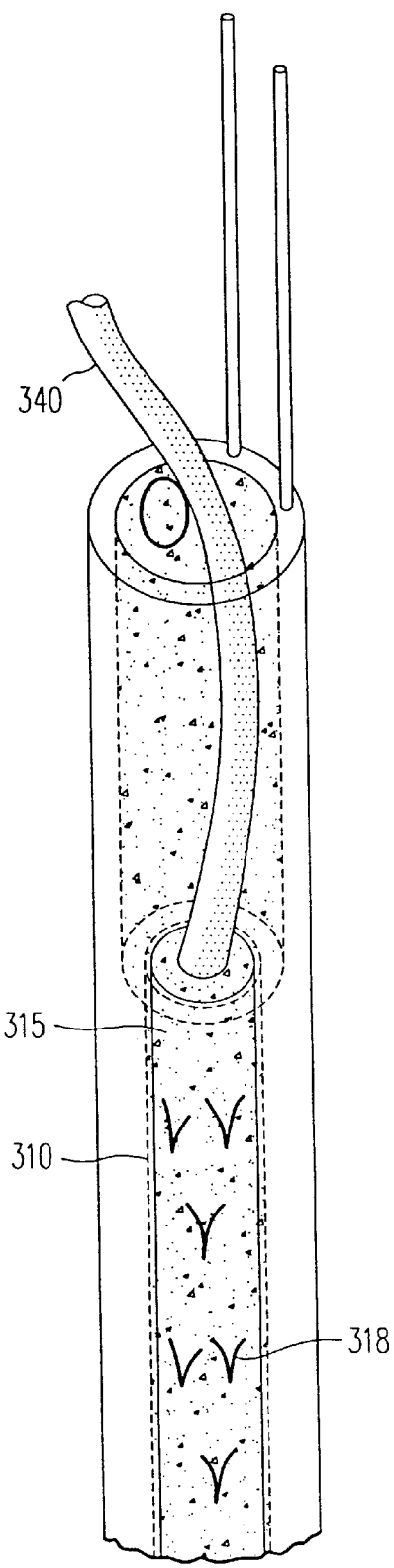
FIG. 10B is a view of a Type "D" fastener with a single leg that may be adapted as a suture anchor.

4. Type "D" Electrical Discharge Fastener. FIGS. 10A–10B show an exemplary Type "D" system 305 with fastener body 310 and introducer 323. The Type "D" embodiment is an "arrow-type" fastener that is adapted for very small fastener diameters, e.g, a little as about 0.50 mm. (not limiting). The length may be any suitable length, for example up to 15 mm. to 20 mm. for a mensical repair. This embodiment operates identically to the Type "A" embodiment and differs in that the fastener body 310 has a proximal head portion 215 that has substantially the same cross section as the distal penetrating portion 316 and therefore the fastener serves more or less as a projectile to secure tissues together. Opposing barbed portions 318 may be added to both the proximal and distal portions 315 and 316 as shown in FIG. 10A. In this embodiment, the entire fastener 310 may be immersed in captured fluid volume 321 in the channel 324 within the introducer with the fluid volume in contact with electrodes 40A and 40B as described above. This embodiment has a different means of sealably maintaining the captured fluid volume 321 in the introducer. A thin burstable element 330 such as bioabsorbable film is cemented over the distalmost end 333 of the introducer 323 to seal the fluid W within chamber 324. Upon actuation of the electrical source 50, the fastener then penetrates through the burstable element 330. FIG. 10C show that a variation of fastener body 310 that carries a suture 340 from its proximal head 315 and therefore the system can be used as a suture anchor.

Alternative embodiments of the introducer of the invention are possible, for example an introducer body similar to that of FIG. 1 that has a deflectable or hinged portion to allow the axis 15 along which a fastener is deployed to be from 0° to 180° from the axis of the introducer (not shown). The electrical discharge fastening system disclosed herein allows for a simple and inexpensive articulatable introducer since no moving mechanical components for driving the fastener are required within any hinge portion. An alternative embodiment of an electrical discharge fastener system utilizes an introducer (not shown) with a working end that has moveable first and second tissue-engaging elements for capturing tissue therebetween as in an Endo-GIA or a circular anastomotic stapler. In this embodiment a plurality of micro-fasteners of the types described above would be carried in the first tissue-engaging element and connected to the electrical energy source. The second tissue-engaging elements would serve the purpose of an anvil for bending the malleable legs of the micro-fasteners that are driven against it. In operation, the trigger mechanism would be actuated to simultaneously fire the plurality of micro-fasteners through the captured tissue. In a related version, the controller may be adapted to fire the fasteners in a timed sequence which may provide additional advantages. In another related version, the controller may be adapted to fire only a few of the fasteners to tack the tissue together for inspection. Thereafter, another signal can be sent by the operator to fire the bulk of the micro-fasteners to complete the tissue fastening procedure. Further, in this type of device, the second signals may be sent at a high or lower power level to optimize the micro-fastener penetration. These options may prove very useful in vessel anastomosis and other procedures in which prior art staplers offer only a one-time chance at correct setting for mechanically driving staples. In each of these embodiments, each micro-fastener would be provided with an independent set of lead wires to selectively actuate each fastener.

Those skilled in the art will appreciate that the exemplary embodiments and descriptions thereof are merely illustrative of the invention as a whole. Accordingly, the present invention is not limited to the specific embodiments described herein, but rather is defined by the scope of the appended claims. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A surgical fastener for penetrating into or through anatomic structures, comprising:
 a fastener body having a proximal head portion and a distal penetrating leg portion; and
 a captured fluid volume proximal to said head portion of the fastener body.

2. The surgical fastener of claim 1 further comprising $1^{st}$ and $2^{nd}$ conductive electrodes proximate to the captured fluid volume.

3. The surgical fastener of claim 2 further comprising a remote electrical source operatively coupled to the $1^{st}$ and $2^{nd}$ electrodes.

4. The surgical fastener of claim 3 wherein the electrical source is capable of selectively delivering from about 50 volts to 10,000 volts to the $1^{st}$ and $2^{nd}$ electrodes.

5. The surgical fastener of claim 3 further comprising a controller for selecting a particular power level to be delivered to the $1^{st}$ and $2^{nd}$ electrodes.

6. The surgical fastener of claim 1 wherein said proximal head portion is at least partly of bioabsorbable material.

7. The surgical fastener of claim 1 wherein said distal penetrating portion is at least partly of bioabsorbable material.

8. The surgical fastener of claim 1 wherein the captured fluid volume and the fastener body are carried in an elongate channel of an elongate member.

9. The surgical fastener of claim 1 wherein the captured fluid volume is of sterile water.

10. The surgical fastener of claim 1 wherein the captured fluid volume is selected from the class of liquids, gels and gases.

11. The surgical fastener of claim 1 wherein the distal penetrating portion comprises at least one sharp-tipped leg.

12. The surgical fastener of claim 8 wherein the elongate member is of transparent material.

13. A method of driving a surgical fastener into or through targeted anatomic structures, comprising the steps of:
 (a) providing a fastener system comprising a proximal captured fluid volume component and distal fastener body component, both components carried in an axial introducer channel having an open distal termination;
 (b) positioning the open distal termination of the introducer proximate to a targeted body structure; and
 (c) causing a high intensity electrical discharge between $1^{st}$ and $2^{nd}$ electrodes and across or within the captured fluid volume to causes explosive vaporization of at least a portion of the captured fluid volume thereby applying axial forces on the fastener body driving the body outward from the introducer channel and into or through the targeted structure.

14. The method of claim 13 wherein the fastener body in step (a) carries a suture.

15. A surgical fastener for penetrating into or through a targeted anatomic structure, comprising:
 a proximal fastener portion and a distal fastener portion that extend along a longitudinal axis and define an interface therebetween;
 wherein said proximal and distal fastener portions are detachably mated to one another generally about said interface;

a fluid-filled chamber carried within said proximal fastener portion; and at least one longitudinally-extending penetrating leg carried by said distal fastener portion.

16. The fastener system of claim 15 wherein the interface is generally transverse to said longitudinal axis.

17. The fastener system of claim 15 wherein the distal fastener portion has a proximal head coupled to the at least one longitudinally-extending leg and said interface is generally at the head of the distal fastener portion.

18. The fastener system of claim 15 wherein the fluid-filled chamber has proximal and distal chamber ends, and the distal chamber end is proximate to the head of said distal fastener portion.

19. The fastener system of claim 15 wherein the fluid-filled chamber is defined within thin walls of the proximal fastener portion.

20. The fastener system of claim 15 wherein the thin walls of the proximal fastener portion are a friable composition.

21. The fastener system of claim 15 wherein the thin walls of the proximal fastener portion are of a bioabsorbable composition.

\* \* \* \* \*